(12) United States Patent
Abramovich et al.

(10) Patent No.: US 8,641,276 B2
(45) Date of Patent: Feb. 4, 2014

(54) SEALED SENSOR SYSTEMS, APPARATUSES AND METHODS

(75) Inventors: Mark Abramovich, Brooklyn, NY (US); Valeriy Armencha, Brewster, NY (US); Stan Mandelkern, Teaneck, NJ (US)

(73) Assignee: Sirona Dental, Inc., Long Island City, NY (US)

( * ) Notice: Subject to any disclaimer, the term of this patent is extended or adjusted under 35 U.S.C. 154(b) by 270 days.

(21) Appl. No.: 13/189,424

(22) Filed: Jul. 22, 2011

(65) Prior Publication Data

US 2013/0022175 A1    Jan. 24, 2013

(51) Int. Cl.
*A61B 6/14*    (2006.01)
*H05G 1/64*    (2006.01)

(52) U.S. Cl.
USPC .............................. 378/191; 378/38; 378/98.8

(58) Field of Classification Search
USPC ............. 378/38–40, 167–170, 177, 189–191, 378/204, 205, 208, 210, 98.8; 433/25, 29, 433/49, 80, 140, 141, 215, 229
See application file for complete search history.

(56) References Cited

U.S. PATENT DOCUMENTS

| 5,619,992 | A | 4/1997 | Guthrie et al. ................. 128/633 |
| 5,677,537 | A * | 10/1997 | Pfeiffer ..................... 250/370.09 |
| 5,912,942 | A | 6/1999 | Schick et al. |
| 6,030,119 | A | 2/2000 | Tachibana et al. |
| 6,350,232 | B1 | 2/2002 | Hascoet et al. |
| 6,549,794 | B1 | 4/2003 | Nadeau, Jr. et al. |
| 6,811,312 | B2 | 11/2004 | Bratslavsky et al. |
| 6,924,486 | B2 | 8/2005 | Schick et al. |
| 7,070,326 | B2 * | 7/2006 | Manley ......................... 378/168 |
| 7,193,219 | B2 | 3/2007 | Schick et al. |
| 2002/0166946 | A1 | 11/2002 | Iizuka et al. |
| 2007/0198073 | A1 | 8/2007 | MacDonald et al. |
| 2010/0107398 | A1 | 5/2010 | Girard ............................ 29/525 |
| 2011/0051903 | A1 | 3/2011 | Armencha et al. |

FOREIGN PATENT DOCUMENTS

WO    WO 96/31155 A1    10/1996
WO    WO 2013/014117 A1    1/2013

OTHER PUBLICATIONS

PCT International Search Report, dated Oct. 29, 2010 in corresponding International Application No. PCT/US2010/047640.
Written Opinion of the International Searching Authority, dated Oct. 29, 2010 in corresponding International Application No. PCT/US2010/047640.

* cited by examiner

*Primary Examiner* — Anastasia Midkiff
(74) *Attorney, Agent, or Firm* — Fitzpatrick, Cella, Harper & Scinto

(57) ABSTRACT

A sensor that is at least partially covered by a sheath, and a positioning arm that is electrically coupled to the sensor, and arranged outside of the sheath, such that a hygienic barrier is formed around the sensor. The sensor is used for filmless dental radiography and the positioning arm enables positioning of the sensor in a patient's mouth. The positioning arm includes a contact that pierces the sheath and establishes an electrical connection with the sensor when the positioning arm is coupled to the sensor.

21 Claims, 6 Drawing Sheets

SEALED SENSOR SYSTEMS, APPARATUSES AND METHODS

BACKGROUND

1. Field

Example aspects described herein generally relate to filmless dental radiography, and, in particular, to filmless dental radiography that involves the use of sealed sensors.

2. Description of Related Art

In the last several decades, the field of filmless dental radiography has emerged. In filmless dental radiography, an x-ray beam is projected through a patient's tooth, but no photographic film is used. Instead, an electronic sensor is placed in the patient's mouth behind the tooth to be examined, and an x-ray beam is projected through the tooth and onto the sensor. The electronic sensor may include a charge-coupled device (CCD), a complementary metal-oxide semiconductor (CMOS) active pixel sensor (APS) array or any other filmless radiation sensor. The x-rays pass through the tooth and impinge on the electronic sensor, which converts the x-rays into an electrical signal. The electrical signal is transmitted to a computer, either directly or through a module containing intermediate processing circuitry. The computer then processes the signal to produce an image on an associated output device, such as a monitor or a printer.

Because electronic sensors, unlike film, are re-usable from patient to patient, it is common to use an x-ray permeable sheath that surrounds the sensor. For example, U.S. Pat. No. 6,811,312 depicts a sheath 12 that surrounds a sensor 10 and a cable 14, and a holder 16 that is used to position the sensor 10 in the patient's mouth. Such sheaths are typically disposable, and are changed between examinations, so that no sheath is used for more than one patient. In this manner, the sheath protects the re-usable sensor from contamination.

However, sheaths that are typically used with sensors may cause gagging and other patient discomfort to the patient in whose mouth the intraoral sensor is placed.

Moreover, the connection between the sensor and the processing module or computer is most conventionally made via a cable. Such a cable, however, can be uncomfortable for, and annoying to, the patient in whose mouth the intraoral sensor is placed. The cable is also bothersome to the dental practitioner when positioning the sensor in the patient's mouth.

In addition, the repeated acts of positioning and re-positioning the cable, which involve a good deal of bending, twisting and pulling of the cable, puts mechanical stresses on the cable. These stresses may eventually lead to cable failure, and indeed cable-related malfunctions are common reasons for product failures and returns in this field.

SUMMARY

The foregoing is addressed by providing a sheath that at least partially covers a sensor, and a positioning arm that is electrically coupled to the sensor.

In accordance with an example aspect herein, a sensor system includes a sensor that is at least partially covered by a sheath, and a positioning arm that is electrically coupled to the sensor, and arranged outside of the sheath, such that a hygienic barrier is formed around the sensor.

In accordance with another example aspect herein, a sensor system includes a sensor and a sheath that at least partially covers the sensor, wherein the sensor is configured to electrically couple to a positioning arm arranged outside of the sheath, such that a hygienic barrier is formed around the sensor.

In accordance with yet another example aspect herein, a positioning arm includes at least one sensor connector, a positioning member, and at least one device interface, wherein the at least one sensor connector is configured to electrically couple to a sensor that is at least partially covered by a sheath such that the at least one sensor connector is arranged outside of the sheath to form a hygienic barrier around the sensor.

In accordance with yet another example aspect herein, a sheath includes a barrier defining an interior portion that conforms to a shape of a sensor, the barrier having an opening constructed to receive the sensor, wherein after receiving the sensor, the barrier covers the sensor and conforms to the shape of the sensor, and the opening of the barrier is sealed, wherein a positioning arm is mechanically and electrically coupled to the sensor, and arranged outside of the barrier, such that the sensor is hygienically sealed by the barrier.

In accordance with yet another example aspect herein, a method for forming a hygienic barrier around a sensor includes covering the sensor at least partially with a sheath that conforms to a shape of the sensor, and electrically coupling a positioning arm to the sensor such that the positioning arm is arranged outside of the sheath to form a hygienic barrier around the sensor.

In accordance with yet another example aspect herein, the sensor is used for filmless dental radiography, the positioning arm enables positioning of the sensor in a patient's mouth, and the positioning arm is arranged on a side of the sensor that faces the patient's teeth, when the sensor is positioned in the patient's mouth. The sensor is sealed by the sheath and the positioning arm includes a contact. The contact pierces the sheath and establishes an electrical connection with the sensor when the positioning arm is coupled to the sensor. The positioning arm is mechanically coupled to the sensor by one of snap-action and cam-action.

In accordance with yet another example aspect herein, the device interface of the positioning arm communicatively couples the sensor connector of the positioning arm to one or more processing devices that are constructed to process electrical signals generated by the sensor and communicated via the positioning arm.

Further features and advantages, as well as the structure and operation, of various example embodiments are described in detail below with reference to the accompanying drawings.

BRIEF DESCRIPTION OF THE DRAWINGS

The features and advantages of the example embodiments will become more apparent from the detailed description set forth below when taken in conjunction with the drawings.

DETAILED DESCRIPTION

Example aspects described herein relate to methods, apparatuses, and systems for sealing sensors used for filmless dental radiography. In an example embodiment, a protective sheath at least partially covers the sensor to provide a hygienic barrier between the sensor and a patient's oral cavity. A positioning arm that is used to position the sensor in the patient's mouth is arranged outside of the sheath, and the positioning arm is electrically coupled to the sensor. The positioning arm is arranged and coupled to the sensor such that a hygienic barrier is formed around the sensor. The conforming sheath helps reduce gagging and other patient discomfort.

The positioning arm includes a sensor connector, a device interface and a positioning member. The sensor connector mechanically and electrically couples the positioning arm to the sensor. The device interface communicatively couples the positioning arm to one or more processing devices that are constructed to process electrical signals generated by the sensor. The positioning member is used to position the sensor in the patient's mouth. The positioning member includes a conductive element that electrically couples the sensor connector and the device interface to each other. In the example embodiment, the positioning member insulates the conductive element. Electrical signals generated by the sensor are communicated to at least one processing device via the communicative coupling formed by the sensor connector, the conductive element, and the device interface.

The device interface communicatively couples the positioning arm to at least one processing device via a wired or wireless link, such as, for example, an electrical coupling through a cable or other electrical conducting element, a wireless communication interface, and the like. In the example embodiment, the device interface is bi-directional.

By virtue of the foregoing arrangement, the sensor can be communicatively coupled to the processing device without the use of a cable that is directly attached to the sensor. Therefore, patient discomfort may be reduced when placing the sensor in a patient's mouth, and positioning of the sensor in the patient's mouth may be improved.

Example processing devices include a computer, an interface board in a computer, an intermediate processing module, or any other device that includes a processor and that is constructed to process the signal generated by the sensor to produce an image on an associated output device, such as a display device or a printer.

The processing device performs control and processing functions, which may include, among other things, controlling the operation of the sensor, reading out data from the sensor, effecting analog-to-digital conversion, executing an event detection algorithm, and processing data read-out of the sensor into a form suitable for output, such as, for example, output to a display device, a printer, or the like.

Figure 1:
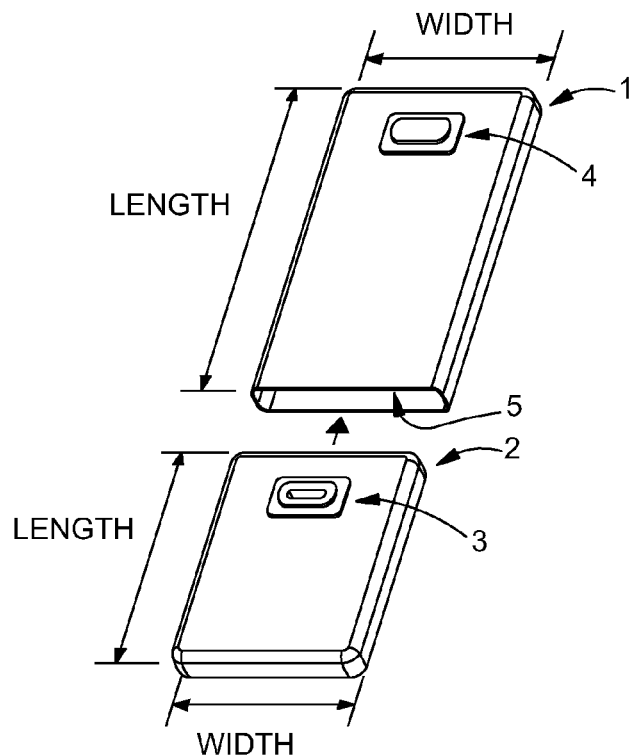
FIG. 1 is a perspective diagram of a sheath and a sensor in accordance with an example embodiment herein.

FIG. 1 shows a sheath 1 and a sensor 2 according to an example embodiment. In the example embodiment, sheath 1 is constructed from a thermoplastic resin which is transparent, disposable, infection resistant, resilient, biocompatible, safe and effective. In other embodiments, the sheath may be constructed from any other suitable type of material. Some examples of materials used to construct sheath 1 include plastic films (such as polyethylene, cellulose, vinyl, PVC and the like), thermoplastic elastomers, silicones, rubbers, synthetic paper (such as Tyvek® and the like), cotton, sponge, latex, nylon, or any other suitable non-toxic radiolucent substance or material permitted by a regulatory body for invasive use. Other synthetic or non-synthetic materials may be used as well.

In the example embodiment, sensor 2 is an electronic intraoral sensor constructed for use in filmless dental radiography. Sensor 2 is constructed to absorb x-ray beams that are projected onto the sensor 2, and to generate electrical signals in response to the absorption of the x-ray beams. In an example embodiment, the sensor 2 includes a conversion material, such as, for example, a scintillator for converting x-ray to light. In this case, the light is collected with an imaging device such as, for example, a CCD or CMOS with light sensitive elements. Such an image sensor is described in U.S. Pat. No. 5,912,942, the contents of which are incorporated by reference herein. In another embodiment, the sensor 2 includes a photoconductor for converting x-rays directly to charges, which are then collected by a charge-sensitive array.

Figure 5:
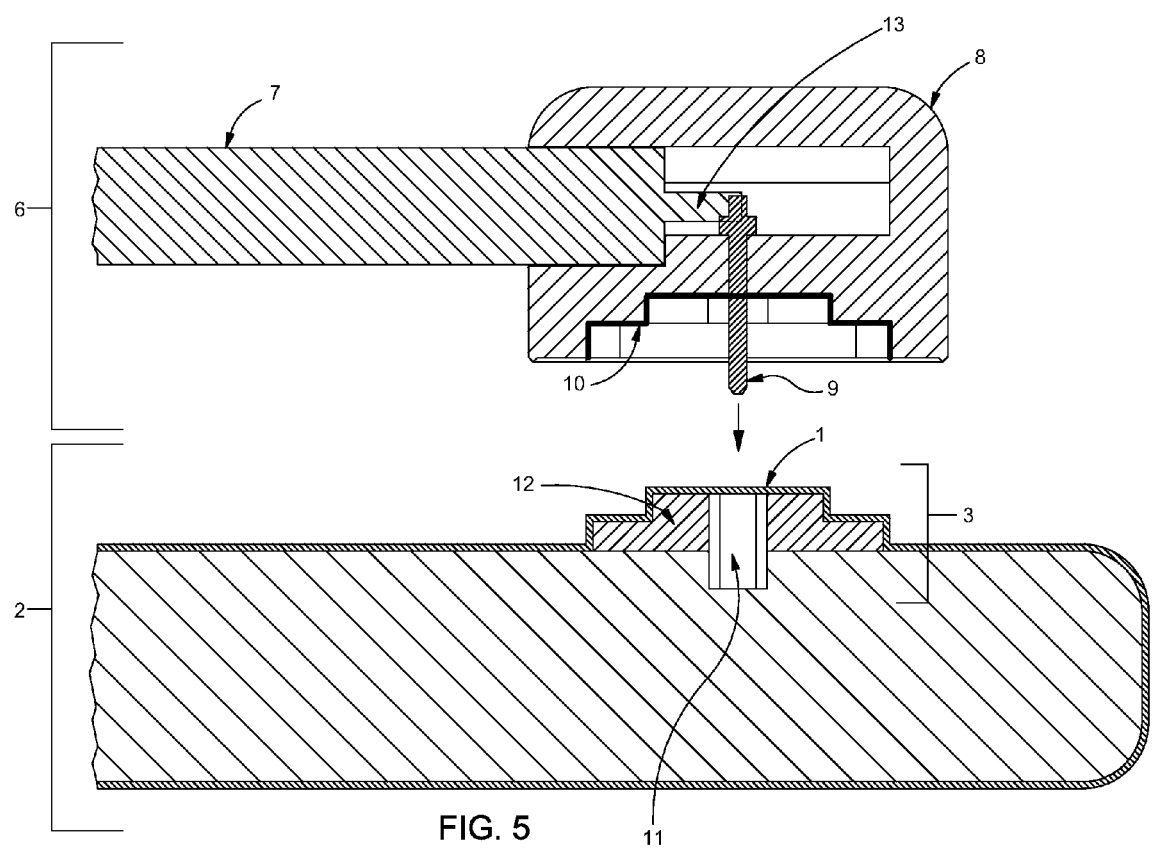
FIG. 5 is a schematic view of the positioning arm.
Figure 7:
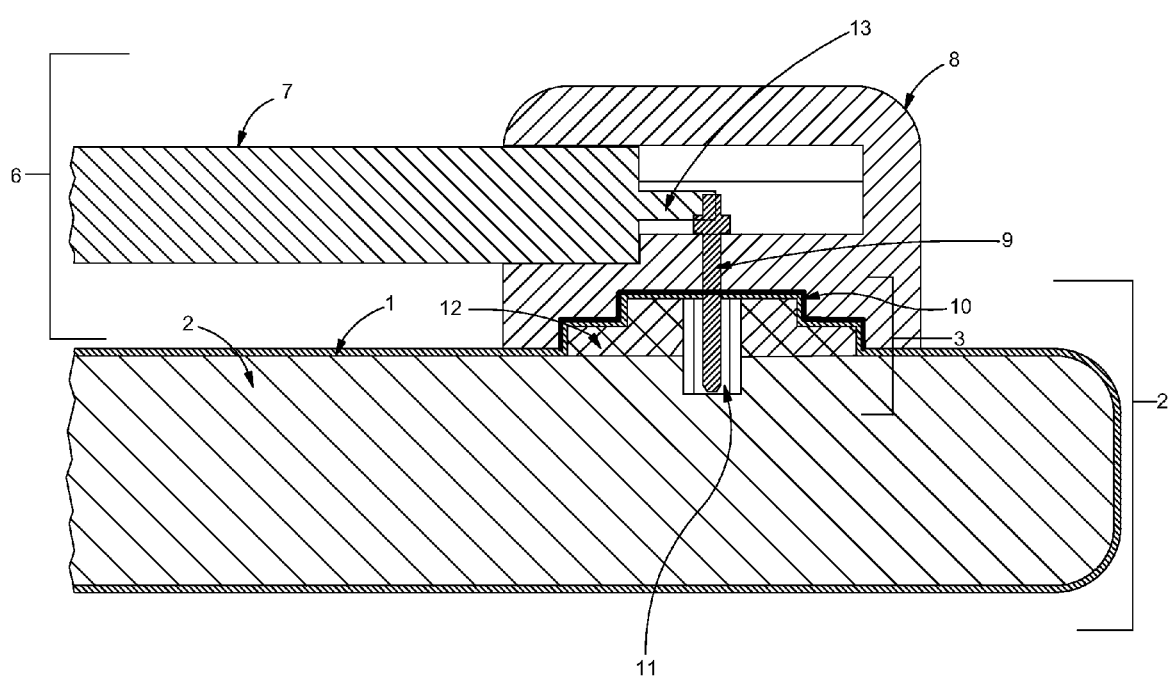
FIG. 7 is a schematic view showing the positioning arm attached to the sealed sensor.

Sensor 2 has a connector 3 that is constructed to mechanically and electrically couple with a positioning arm 6 of FIGS. 5 and 7. In the example embodiment, connector 3 is arranged on a side of sensor 2 that faces the patient's teeth, when the sensor is positioned in the patient's mouth. In the example embodiment, the connector 3 is a snap-action connector constructed to mechanically and electrically couple with the positioning arm by snap-action, without the use of a tool. In other embodiments the connector can be constructed to mechanically and electrically couple with the positioning arm with the use of a tool. In other embodiments, the connector can be a cam-action connector constructed to mechanically and electrically couple with the positioning arm by cam-action, either with or without the use of a tool.

As shown in FIG. 1, sheath 1 generally conforms to the shape of sensor 2. In particular, sheath 1 has a width and thickness that conforms to the width and thickness of sensor 2. Sheath 1 has a connector portion 4 that conforms to the shape of connector 3. In the example embodiment depicted, the length of sheath 1 is longer than the length of sensor 2, however, in other embodiments, the length of sheath 1 can conform to the length of sensor 2, or even be shorter than sensor 2. Sheath 1 forms a continuous barrier with an opening 5 at one end. Sensor 2 is inserted into sheath 1 via opening 5.

Figure 2:
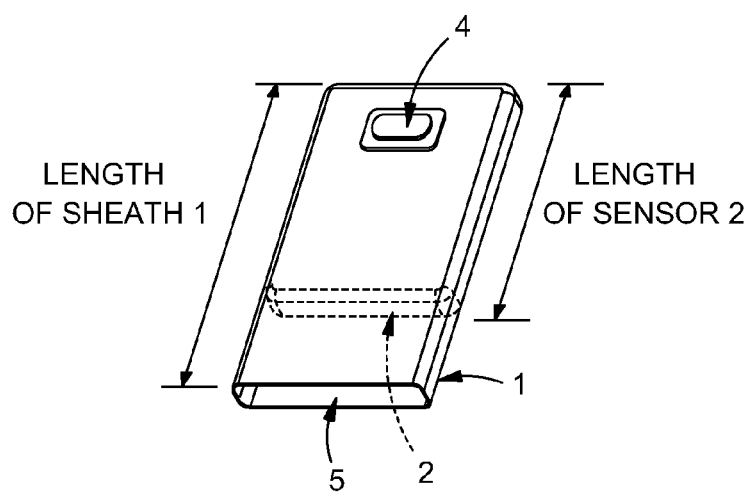
FIG. 2 is a perspective diagram of the sensor after being inserted into the sheath.

FIG. 2 shows sensor 2 after being inserted into sheath 1 via opening 5. As can be appreciated in view of FIGS. 1 and 2, connector portion 4 of sheath 1 is aligned with connector 3 of sensor 2, and the length of sheath 1 extends past the length of sensor 2, when the sensor 2 is inserted into sheath 1 as represented in FIG. 2. Sheath 1 forms a continuous barrier around sensor 2, with opening 5 at one end. In the example embodiment, heat is applied to sheath 1 to seal opening 5 by using a heat sealer, such as, for example, a heat iron, a heat gun, or the like. During the heat-sealing process, the length of sheath 1 shrinks such that it conforms to the length of sensor 2. Part or all of any excess portion of sheath 1 that extends beyond the length of sensor 2 can be trimmed before (or after) heat-sealing is performed. In other embodiments, any excess portion of sheath 1 that extends beyond the length of sensor 2 is trimmed so that the length of sheath 1 conforms to the length of sensor 2, and opening 5 is sealed with tape.

Figure 3:
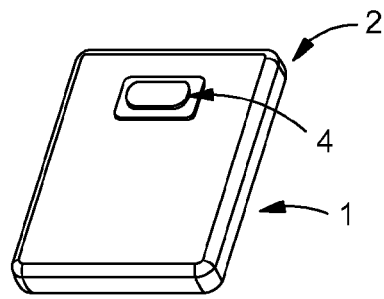
FIG. 3 is a perspective diagram of the sealed sensor.

FIG. 3 shows the sealed sensor 2 after the opening of the sheath 1 has been sealed. As shown in FIG. 3, the length of sheath 1 conforms to the length of sensor 2, and sheath 1 forms a hygienic barrier around the sensor 2.

Figure 4:
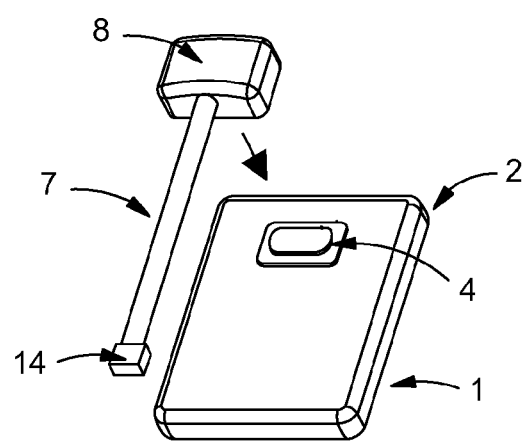
FIG. 4 is a perspective view showing a positioning arm, in accordance with an example embodiment herein.

FIG. 4 is a perspective view showing the positioning arm (6 of FIG. 5) before it is mechanically and electrically coupled with connector 3 of sealed sensor 2. As shown in FIG. 4, the positioning arm includes positioning member 7, sensor connector 8, and device interface 14. FIG. 5 is a schematic view showing the positioning arm (6 of FIG. 5) before coupling with connector 3 of the sealed sensor 2. In the example embodiment, the positioning arm is a rigid positioning arm, but in other embodiments, the positioning arm can be a flexible, or partly flexible, positioning arm.

As shown in FIG. 5, the positioning arm 6 includes positioning member 7 and sensor connector 8. Positioning arm 6 also includes a device interface (14 of FIG. 4). In the example embodiment, the device interface 14 is arranged at an end of positioning arm 6 opposite from the end at which the sensor connector 8 is arranged (although in other embodiments, it can be positioned elsewhere on positioning arm 6 and/or sensor connector 8). The device interface 14 communicatively couples the positioning arm 6 to a processing module or a computer (not shown in FIG. 5), as described below with respect to FIGS. 9 and 10. Sensor connector 8 is attached or otherwise coupled to positioning member 7.

In other embodiments, sensor connector 8 is attached or otherwise coupled to the device interface 14 directly, without the use of positioning member 7. In such embodiments, the device interface 14 is arranged adjacent to sensor connector 8, or included in sensor connector 8, and the device interface 14 communicatively couples the sensor connector 8 to a processing module or a computer (not shown in FIG. 5).

Sensor connector 8 includes contact 9 and sealing member 10. In other example embodiments, the sealing member 10 can be separate from positioning arm 6. In the example embodiment, positioning member 7 is rigid. Sealing member 10 surrounds contact 9. Positioning member 7 is attached to sensor connector 8 such that positioning member 7 is mechanically and electrically coupled with contact 9 via a conductive element 13. Contact 9 protrudes from sensor connector 8. Positioning arm 6 is constructed such that contact 9 pierces sheath 1 of sealed sensor 2 when positioning arm 6 is mechanically and electrically coupled with connector 3 of sealed sensor 2. In the example embodiment, sealing member 10 is a molded sealing lip. In other embodiments, the sealing member 10 can be a gasket or O-ring.

As shown in FIG. 5, connector 3 of sealed sensor 2 includes receptacle 11 constructed to receive contact 9 of positioning arm 6, thereby forming an electrical connection between sensor 2 and positioning arm 6. In the example embodiment, contact 9 and receptacle 11 are both constructed from a conductive material, and when receptacle 11 receives contact 9, contact 9 touches a surface of receptacle 11, thereby forming the electrical connection between sensor 2 and positioning arm 6. In the example embodiment, connector 3 also includes a connection protrusion 12 that protrudes past the surface of sensor 2. The molded sealing lip 10 of positioning arm 6 has a shape that conforms to the shape of connection protrusion 12 of connector 3. Molded sealing lip 10 is constructed to receive connection protrusion 12, thereby forming a mechanical connection between sensor 2 and positioning arm 6. In the example embodiment, positioning member 7 and sensor connector 8 are constructed using a non-conductive thermoplastic resin, such as, for example, PC, PC/ABS, polypropaline, polyethelyne, or the like. However, in other embodiments, other materials can be used to construct the positioning member 7 and the sensor connector 8. Moreover, in other embodiments, positioning member 7 is a flexible cable whose cable jacket is formed from an insulating material, such as polyeurethene, or the like.

Figure 6:
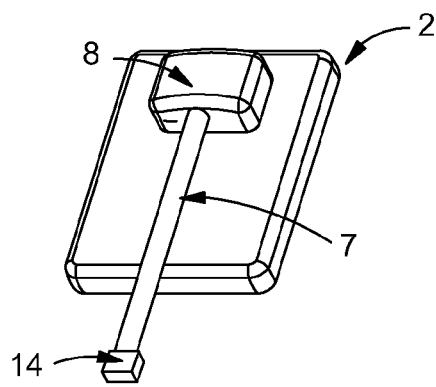
FIG. 6 is a perspective view showing the positioning arm attached to the sealed sensor.

FIG. 6 is a perspective view showing the positioning arm (6 of FIG. 5) after it is mechanically and electrically coupled with connector 3 of sealed sensor 2 and pierces sheath 1, and FIG. 7 is a schematic view showing positioning arm (6 of FIG. 5) after coupling with connector 3 of the sealed sensor 2.

As shown in FIG. 7, when positioning arm 6 is mechanically attached to sensor 2 by snap-action via molded sealing lip 10 and connection protrusion 12, contact 9 pierces sheath 1 and establishes an electrical connection with receptacle 11 of sensor 2. Also, when positioning arm 6 is mechanically attached to sensor 2, molded sealing lip 10 is compressed against the sheath 1 and provides a seal around connection protrusion 12 and receptacle 11, re-establishing a complete hygienic barrier around sensor 2.

Figure 8:
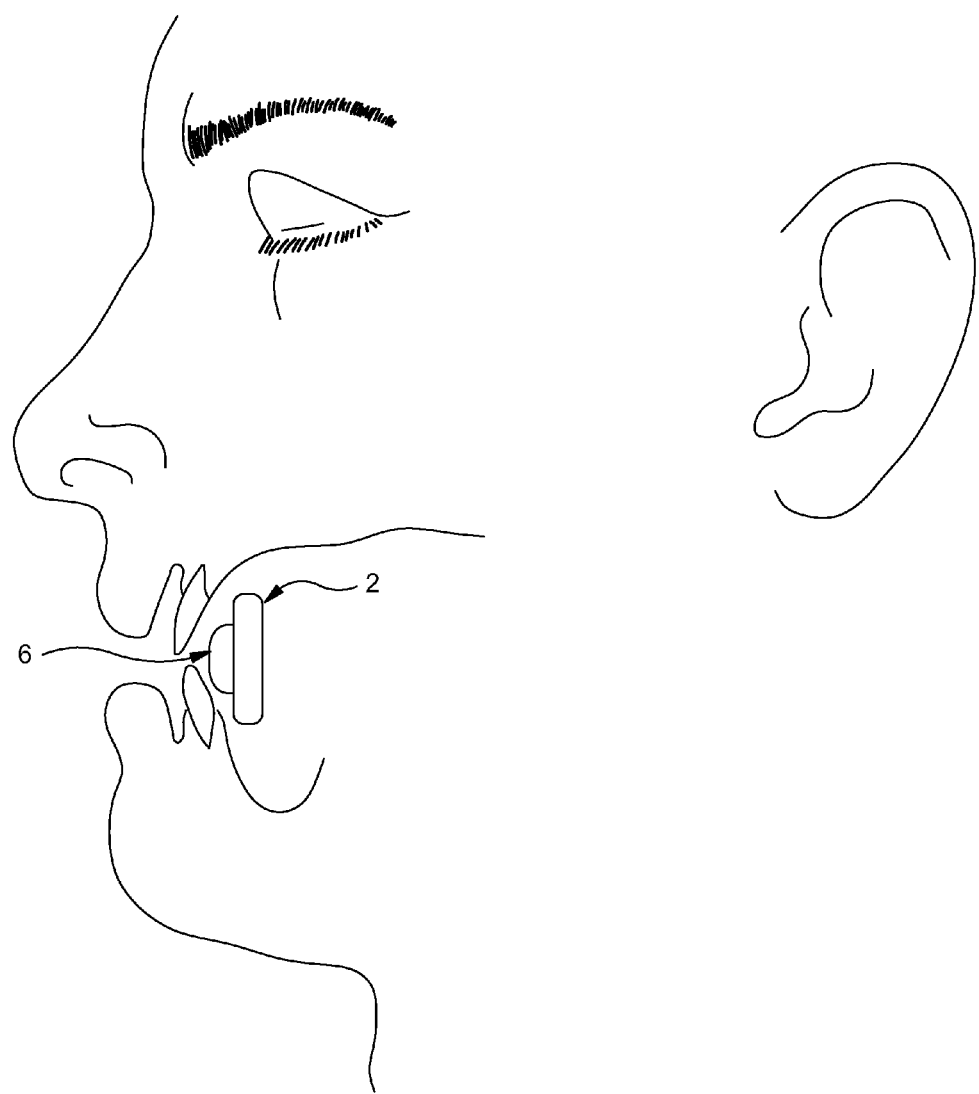
FIG. 8 is a diagram showing the positioning of the sealed sensor in a patient's mouth.

FIG. 8 is a diagram showing an example of positioning of the sealed sensor 2 in a patient's mouth. As shown in FIG. 8, the sensor 2 is positioned in the patient's mouth behind the patient's teeth, and the positioning arm 6 is arranged on the side of the sensor 2 that faces the patient's teeth.

Figure 9:
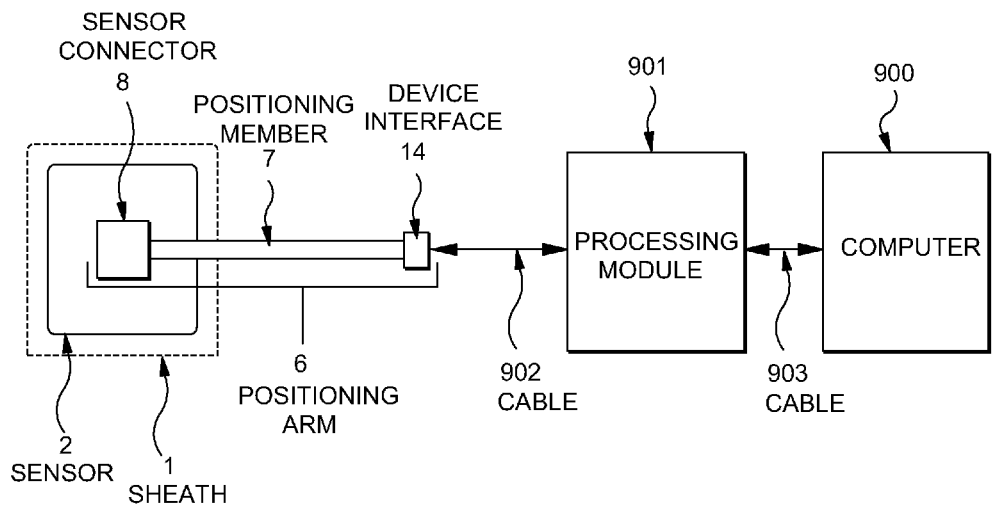
FIG. 9 is a block diagram of the sealed sensor coupled to a processing device, in accordance with an example embodiment herein.

FIG. 9 is a block diagram of an embodiment in which the sealed sensor 2 is coupled to computer 900 via processing module 901. As shown in FIG. 9, positioning member 7, sensor connector 8 and device interface 14 form at least part of positioning arm 6. The device interface 14 is arranged at an end of positioning member 7 opposite from the end at which the sensor connector 8 is arranged, in this example. The device interface 14 is a device interface that communicatively couples the positioning arm 6 to processing module 901 via a link, such as, for example, a wired link provided by cable 902. In an example embodiment, cable 902 is a USB cable, device interface 14 includes a micro USB connector that connects to one end of USB cable 902, and processing module 901 includes a USB port that connects to the other end of USB cable 902. In other embodiments, the device interface 14 can communicatively couple the positioning arm 6 to processing module 901 via any suitable type of wired or wireless link.

As shown in FIG. 9, sensor 2 is surrounded by sheath 1. Sensor connector 8 of positioning arm 6 is mechanically and electrically coupled with connector 3 (not shown in FIG. 9) of sealed sensor 2, as described above with respect to FIG. 7. When sensor connector 8 is arranged on top of connector 3, the connector 3 is not visible. Specifically, positioning arm 6 is mechanically attached to sensor 2 by snap-action via the molded sealing lip 10 of sensor connector 8 and the connection protrusion 12 of connector 3 (not shown in FIG. 9). When positioning arm 6 is mechanically attached to sensor 2, the contact 9 of sensor connector 8 pierces sheath 1 and establishes an electrical connection with the receptacle of connector 3.

Electrical signals are conveyed to and from the electronic sensor 2 via positioning arm 6. The electrical signals may be, for example, electronic information signals and/or electrical power. Processing module 901 is communicatively coupled to computer 900 via a link, such as, for example, a wired link provided by cable 903. In an example embodiment, cable 903 is a USB cable, processing module 901 includes a USB connector that connects to one end of USB cable 903, and computer 900 includes a USB port that connects to the other end of USB cable 903. In other embodiments, the processing module 901 can be communicatively coupled to the computer 900 via any suitable type of wired or wireless link that provides bi-directional communication between processing module 901 and computer 900. For example, such a link may be provided by at least one of a PCI slot, an ISA slot, a USB port, a wireless interface (e.g., Bluetooth, WiFi), a near field transceiver, an optical transceiver, and the like.

In operation, the positioning arm 6 is used to position the sensor 2 in a patient's mouth behind the teeth to be examined, and an externally generated x-ray beam is projected from outside the mouth through the tooth or teeth and onto the sensor 2. Electrical signals generated by the sensor 2 in response to the beam are communicated to processing module 901 via device interface 14 of positioning arm 6.

By virtue of the foregoing arrangement, the sensor 2 can be communicatively coupled to the processing module 901 without the use of a cable that is directly attached to the sensor 2. Therefore, patient discomfort may be reduced when placing the sensor 2 in a patient's mouth, and positioning of the sensor in the patient's mouth may be improved. Processing module 901 processes the signals generated by the sensor 2 to produce image data that is communicated to computer 900.

Computer 900 receives the image data and can output the image data by using an output device that is coupled with the computer 900, such as, for example, a display device (not shown), a printer (not shown), or an interface to an external network. Processing module 901 also performs control and processing functions, which may include, among other things, one or more of controlling the operation of the sensor 2, reading out data from the sensor 2, effecting analog-to-digital conversion, executing an event detection algorithm, and processing data read-out of the sensor 2 into a form suitable for output, such as, for example, output to a display device, a printer, or the like.

Figure 10:
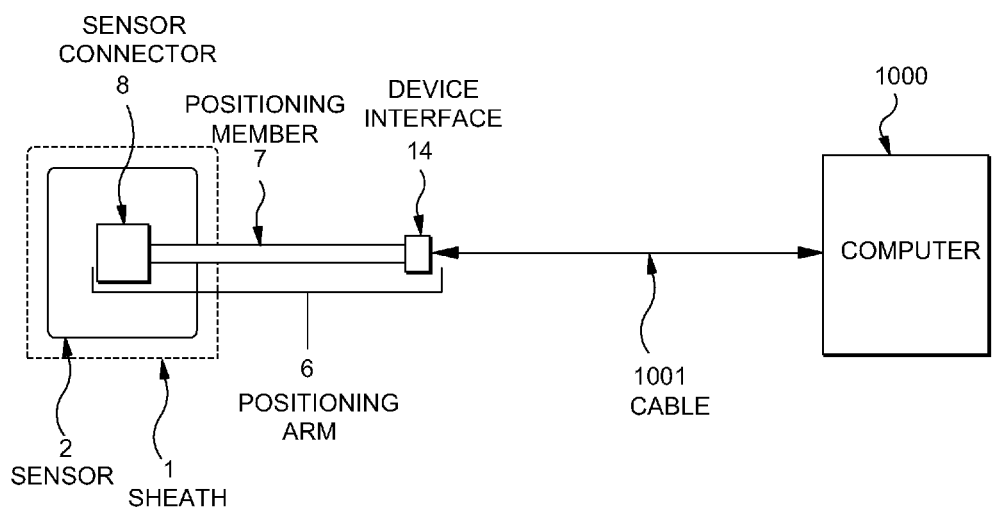
FIG. 10 is a block diagram of the sealed sensor coupled to a processing device, in accordance with an example embodiment herein.

FIG. 10 is a block diagram of an embodiment in which the sealed sensor 2 is coupled to computer 1000 directly by way of device interface 14. In the example embodiment of FIG. 10, the device interface 14 of positioning arm 6 is a device interface that communicatively couples the positioning arm 6 to computer 1000 directly via a link, such as, for example, a wired link provided by cable 1001. In an example embodiment, cable 1001 is a USB cable, device interface 14 includes a micro USB connector that connects to one end of USB cable 1001, and computer 1000 includes a USB port that connects to the other end of USB cable 1001.

In other embodiments, the device interface 14 can communicatively couple the positioning arm 6 to computer 1000 via any suitable type of wired or wireless link. For example, sensor 2 may be coupled to computer 1000 via a PCI slot, an ISA slot, a USB port, a wireless interface (e.g., Bluetooth, WiFi), a near field transceiver, an optical transceiver, or any other suitable type of wired or wireless link.

In operation, the positioning arm 6 is used to position the sensor 2 in a patient's mouth behind the teeth to be examined, and an externally generated x-ray beam is projected from outside the mouth through the tooth or teeth and onto the sensor 2. Electrical signals generated by the sensor 2 in response to the beam are communicated to computer 1000 via device interface 14 of positioning arm 6.

By virtue of the foregoing arrangement, the sensor 2 can be communicatively coupled to the computer 1000 without the use of a cable that is directly attached to the sensor 2. Therefore, patient discomfort may be reduced when placing the sensor 2 in a patient's mouth, and positioning of the sensor in the patient's mouth may be improved.

Computer 1000 processes the signals generated by the sensor 2 to produce image data that can be output by using an output device that is coupled with the computer 1000, such as, for example, a display device (not shown), a printer (not shown), or an interface to an external network. Computer 1000 also performs control and processing functions, which may include, among other things, one or more of controlling the operation of the sensor 2, reading out data from the sensor 2, effecting analog-to-digital conversion, executing an event detection algorithm, and processing data read-out of the sensor 2 into a form suitable for output, such as, for example, output to a display device, a printer, or the like.

Although example aspects of the disclosure have been described in certain specific embodiments, many additional modifications and variations would be apparent to those skilled in the art. It thus should be understood that this disclosure may be practiced in ways other than those specifically described. Thus, the present example embodiments, again, should be considered in all respects as illustrative and not restrictive.

What is claimed is:

1. A sensor system comprising:
    a sensor that is at least partially covered by a sheath; and
    a positioning arm that is electrically coupled to the sensor, and arranged outside of the sheath, such that a hygienic barrier is formed around the sensor,
    wherein the sensor is sealed by the sheath and the positioning arm includes a contact, and wherein the contact pierces the sheath and establishes an electrical connection with the sensor when the positioning arm is coupled to the sensor.

2. The sensor system according to claim 1, wherein the sensor is used for filmless dental radiography, the positioning arm enables positioning of the sensor in a patient's mouth, and the positioning arm is arranged on a side of the sensor that faces the patient's teeth, when the sensor is positioned in the patient's mouth.

3. The sensor system according to claim 1, wherein the sensor is covered by the sheath such that the sheath forms a seal around the sheath.

4. The sensor system according to claim 1, wherein the sensor is completely covered by the sheath.

5. The sensor system according to claim 1, wherein the positioning arm is mechanically coupled to the sensor by one of snap-action and cam-action.

6. The sensor system according to claim 1, wherein the positioning arm is mechanically coupled to the sensor.

7. The sensor system according to claim 1, wherein the positioning arm is rigid.

8. A sensor system comprising:
    a sensor; and
    a sheath that at least partially covers the sensor,
    wherein the sensor is configured to electrically couple to a positioning arm arranged outside of the sheath, such that a hygienic barrier is formed around the sensor,
    wherein the sensor is sealed by the sheath and the positioning arm includes a contact, and
    wherein the contact pierces the sheath and establishes an electrical connection with the sensor when the positioning arm is coupled to the sensor.

9. The sensor system according to claim 8, wherein the sensor includes a connector that is constructed to electrically couple to the positioning arm.

10. The sensor system according to claim 8, wherein the sensor is used for filmless dental radiography, the positioning arm enables positioning of the sensor in a patient's mouth, and the positioning arm is arranged on a side of the sensor that faces the patient's teeth, when the sensor is positioned in the patient's mouth.

11. The sensor system according to claim 8, wherein the sensor is completely covered by the sheath.

12. The sensor system according to claim 8, wherein the positioning arm is mechanically coupled to the sensor by one of snap-action and cam-action.

13. The sensor system according to claim 8, wherein the positioning arm is rigid.

14. A positioning arm comprising:
   at least one sensor connector;
   a positioning member; and
   at least one device interface,
   wherein the at least one sensor connector is configured to electrically couple to a sensor that is at least partially covered by a sheath, such that the at least one sensor connector is arranged outside of the sheath, to form a hygienic barrier around the sensor,
   wherein the sensor is sealed by the sheath and the at least one sensor connector includes a contact, and
   wherein the contact pierces the sheath and establishes an electrical connection with the sensor when the at least one sensor connector is coupled to the sensor.

15. The positioning arm according to claim 14, wherein the sensor is used for filmless dental radiography, the positioning member enables positioning of the sensor in a patient's mouth, and the positioning member and the sensor connector are arranged on a side of the sensor that faces the patient's teeth, when the sensor is positioned in the patient's mouth.

16. The positioning arm according to claim 14, wherein the sensor connector is mechanically coupled to the sensor by one of snap-action and cam-action.

17. The positioning arm according to claim 14, wherein the positioning member is rigid.

18. The positioning arm according to claim 14, wherein the device interface communicatively couples the sensor connector to one or more processing devices that are constructed to process electrical signals generated by the sensor and communicated via the positioning arm.

19. A sheath comprising:
   a barrier defining an interior portion that conforms to a shape of a sensor, the barrier having an opening constructed to receive the sensor,
   wherein after receiving the sensor, the barrier covers the sensor and conforms to the shape of the sensor, and the opening of the barrier is sealed,
   wherein a positioning arm is mechanically and electrically coupled to the sensor, and arranged outside of the barrier, such that the sensor is hygienically sealed by the barrier,
   wherein the sensor is sealed by the sheath and the positioning arm includes a contact, and
   wherein the contact pierces the sheath and establishes an electrical connection with the sensor when the positioning arm is electrically coupled to the sensor.

20. A method of forming a hygienic barrier around a sensor, the method comprising:
   covering the sensor at least partially with a sheath that conforms to a shape of the sensor; and
   electrically coupling a positioning arm to the sensor such that the positioning arm is arranged outside of the sheath to form a hygienic barrier around the sensor,
   wherein the sensor is sealed by the sheath and the positioning arm includes a contact, and
   wherein in the electrically coupling, the contact pierces the sheath and establishes an electrical connection with the sensor.

21. The method according to claim 20, wherein the covering includes inserting the sensor into the sheath via an opening in the sheath, and sealing the opening of the sheath.

* * * * *